(12) United States Patent
Buck et al.

(10) Patent No.: US 8,156,070 B2
(45) Date of Patent: Apr. 10, 2012

(54) INSULIN PUMP PROGRAMMING SOFTWARE WITH BASAL PROFILE PREVIEW FEATURE

(75) Inventors: Schuyler Buck, Muncie, IN (US); Andreas Buhr, Derendingen (CH); Jason Bush, Fishers, IN (US); Robert Hellwig, Bern (CH); David Bradley Markisohn, Indianapolis, IN (US); Leon R. Organ, III, Indianapolis, IN (US)

(73) Assignee: Roche Diagnostics Operations, Inc., Indianapolis, IN (US)

(*) Notice: Subject to any disclaimer, the term of this patent is extended or adjusted under 35 U.S.C. 154(b) by 825 days.

(21) Appl. No.: 12/205,570

(22) Filed: Sep. 5, 2008

(65) Prior Publication Data

US 2010/0064236 A1    Mar. 11, 2010

(51) Int. Cl.
G06F 15/18    (2006.01)
G06F 15/00    (2006.01)

(52) U.S. Cl. .......................................... 706/62
(58) Field of Classification Search .................. 706/62
See application file for complete search history.

(56) References Cited

U.S. PATENT DOCUMENTS

| | | | | |
|---|---|---|---|---|
| 6,977,074 B2* | 12/2005 | Kundig et al. | | 424/93.7 |
| 6,994,851 B1* | 2/2006 | Kundig et al. | | 424/93.7 |
| 7,364,729 B2* | 4/2008 | Kundig et al. | | 424/93.7 |
| 7,815,602 B2* | 10/2010 | Mann et al. | | 604/131 |
| 7,819,843 B2* | 10/2010 | Mann et al. | | 604/131 |
| 7,935,076 B2* | 5/2011 | Estes et al. | | 604/65 |
| 8,088,098 B2* | 1/2012 | Yodfat et al. | | 604/67 |
| 8,114,066 B2* | 2/2012 | Naef et al. | | 604/890.1 |
| 2003/0060765 A1 | 3/2003 | Campbell et al. | | |
| 2006/0123349 A1 | 6/2006 | Wakabayashi | | |
| 2007/0016449 A1 | 1/2007 | Cohen et al. | | |
| 2007/0033074 A1 | 2/2007 | Nitzan et al. | | |
| 2007/0066956 A1 | 3/2007 | Finkel | | |
| 2007/0106135 A1 | 5/2007 | Sloan et al. | | |
| 2007/0112298 A1 | 5/2007 | Mueller, Jr. et al. | | |
| 2007/0239686 A1 | 10/2007 | Quinn-Jacobs | | |
| 2008/0106431 A1 | 5/2008 | Blomquist | | |

FOREIGN PATENT DOCUMENTS

WO    WO 00/60529    10/2000

OTHER PUBLICATIONS

Disetronic, "DiagLog Pump Programming Tool," Reference Manual, ver. 02 (Jun. 2005).
Medtronic Minimed, "Solutions Pumps and Meters Software," Manual, ver7.0 (2005).
Disetronic Medical Systems AG, "Accu-Chek Insulin Pump Configuration Software," User Manual, (2005).
Animans Corporation, "ezManager Plus," User Manual, (2007).

* cited by examiner

*Primary Examiner* — Michael B Holmes
(74) *Attorney, Agent, or Firm* — Faegre Baker Daniels

(57) ABSTRACT

Insulin pump programming software is disclosed that generates thumbnail images of basal rate profile data contained in source files and displays the images to permit an operator to select the desired profile data without opening the source files. The software also permits the operator to verify changes to pump profiles before programming the pump by displaying thumbnail images of the current pump profile and the new pump profile.

24 Claims, 15 Drawing Sheets

INSULIN PUMP PROGRAMMING SOFTWARE WITH BASAL PROFILE PREVIEW FEATURE

FIELD OF THE INVENTION

The present teachings generally relate to programming insulin pumps and more specifically to pump programming software that permits previewing graphic representations of basal rate profiles before accessing the file containing the underlying data or replacing a profile stored on a pump with the represented profile.

BACKGROUND

An insulin pump is a fluid infusion device for delivering insulin to people who suffer from diabetes. The pump, which is worn by the user and eliminates the need for multiple daily insulin injections, closely imitates a normally functioning pancreas by releasing hundreds of small doses of insulin each day into the body through an infusion set to regulate blood glucose levels. The rate of delivery of these small doses (i.e., the basal rate) varies from user to user. Indeed, even for a particular user, the basal rate varies throughout the day, and depends upon a variety of factors such as the user's internal clock, metabolism, physical health, and level of stress and exercise.

A basal rate profile consists of one or more basal rates defined to cover the 24 hours of the day (e.g., 24 hourly basal rates). Many users use different basal rate profiles for different circumstances. For example, one basal rate profile may be used for weekdays, another profile (i.e., with different hourly basal rates) for weekends, and another profile for vacation days. These different basal rate profiles are designed to accommodate the expected differences in the user's background insulin needs resulting from variations in the user's sleep patterns, levels of exercise and stress, health condition, menstrual cycle status, etc. during such periods.

As the amount and rate of insulin delivery (both basal and bolus) must be tailored to the individual needs of the user, modern pumps are programmable. Some pumps are capable of communicating with a separate computing device, and are compatible with software applications that may be executed on the computing device. The software permits an operator, such as the user or a health care provider, to customize the settings of the various parameters that affect the pump's operation. In particular, it is commonly necessary to make adjustments to the basal rate profiles stored in a user's pump. As multiple profiles (i.e., profile sets) are typically stored in a pump as mentioned above, the operator may need to review the data for each of the profiles to decide which profile(s) require modification. Sometimes a single profile requires modification. Other times, entire profile sets require modification. To determine which profiles must be changed on a user's pump, the operator using conventional programming software activates each profile by accessing the file containing the underlying basal rate profile data, and views the data in a tabular or graphical format.

The above-mentioned profile modifications may be accomplished by replacing a profile or set of profiles existing on a pump with profiles (or edited versions of profiles) existing in source files stored on the computing device. An operator, such as a health care provider, may use a computing device that stores many such source files. Accordingly, the operator using conventional programming software must continue to access the various source files to view the underlying data until the operator identifies a source file containing the desired profile. The operator then either edits the profile before using it as a replacement for an existing pump profile, or saves the unedited profile directly to the pump.

In the process of replacing or editing a pump profile, the operator must take care in avoiding any inadvertent changes as unintentional modifications to insulin delivery parameters may directly affect the health of the user. Under delivery of insulin may result in hyperglycemia (high blood glucose levels), which may increase the risk of infection and, if persistent for long periods, may cause damage to the retinas and kidneys, and nerve damage. Over delivery of insulin may immediately lead to hypoglycemia, which may result in seizures, unconsciousness, and other highly undesirable manifestations of low blood glucose levels. Accordingly, conventional programming software incorporates safety features that prompt the operator to review the proposed modifications to pump profiles before the pump is programmed.

As illustrated by the above-described characteristics, insulin pump basal rate profile programming may be a relatively time-consuming, complicated, and error-prone task which, if performed incorrectly, may lead to serious health risks for the pump user. Accordingly, pump programming software should be designed to simplify, to the extent possible, the programming processes while simultaneously incorporating safety measures to prevent operators from inadvertently programming a pump with parameter settings that may harm the user or adversely affect the operation of the pump. Features that facilitate simple, safe pump programming are particularly helpful to health care providers who may be responsible for programming multiple pumps on a regular basis.

SUMMARY

The present teachings provide pump programming software that permits the operator to preview thumbnail images including graphical representations of basal rate profiles, either individual profiles or entire sets of profiles, without having to access the file containing the underlying basal rate data. This preview feature permits the operator to quickly and accurately identify a desired profile for editing and/or for use as a replacement of a profile existing on a user's pump. When an operator is saving a profile to a pump as a replacement of an existing pump profile, the software further provides thumbnail images of the replacement profile and the existing profile to permit the operator to visually confirm the changes about to be made to the existing pump profile.

In an exemplary embodiment of the present disclosure, there is disclosed a method of managing basal rate profiles for use on an insulin pump. The method includes the step of storing a file containing data corresponding to a basal rate profile for use by an insulin pump. The method further includes the step of generating a thumbnail image including a graphical representation of the profile. The method further includes the step of, without opening the file to access the data, simultaneously displaying a file indicator associated with the file and the thumbnail image. The method also includes the step of determining based on the graphical representation of the thumbnail image whether to access the data. Finally, the method includes the step of opening the file to access the data in response to an operator's selection of the profile represented by the thumbnail image. In a variation thereof, the file is stored in a memory location of a computing device. In another variation, the thumbnail image includes a representation of each basal rate in the profile on a graph having a time axis and a units per hour axis. In an extension of this variation, the thumbnail image further includes a total daily basal insulin value. In another variation, the file indicator includes a name of the file. In yet another variation, the file is a configuration file including general configuration data and a plurality of basal rate profiles. In another variation, the file is an individual basal rate profile file. In yet another variation, the thumbnail image is displayed in a preview pane with a plurality of other thumbnail images corresponding to other basal rate profiles. In an extension of this variation, the preview pane includes a scrollbar for browsing the plurality of thumbnail images. In another variation of the disclosed method, the generating step includes the step of receiving a basal insulin calculation input. In an extension of this variation, the thumbnail image represents a standardized basal rate profile modified based on the basal insulin calculation input. In another variation, the file is a profile set file including a plurality of basal rate profiles.

In another exemplary embodiment of the present disclosure, there is disclosed a method of programming basal rate profiles for use on an insulin pump. The method includes the step of retrieving a source file including data corresponding to a first basal rate profile for use by an insulin pump. The method further includes the step of generating a first thumbnail image including a graphical representation of the first profile. The method further includes the step of replacing a target file on an insulin pump corresponding to a second basal rate profile with the source file. In this embodiment, the replacing step includes the step of displaying the first thumbnail image with a second thumbnail image including a graphical representation of the second profile to permit an operator to review differences between the images and provide an input confirming a desire to complete the replacing step. In a variation thereof, the method further includes the step of modifying the source file. In another variation, the replacing step further includes the step of displaying a critical change confirmation dialog box including the first and second thumbnail images when a daily basal insulin total corresponding to the first profile is greater than a daily basal insulin total corresponding to the second profile. In an extension of this variation, the replacing step further includes the step of receiving a second input from the operator confirming a desire to complete the replacing step. In a further extension, the second input is a keyboard entry of the daily basal insulin total corresponding to the first profile.

In yet another exemplary embodiment of the present disclosure, there is disclosed a computer readable medium tangibly embodying a program of instructions executable by a computing device to perform method steps for programming insulin pumps. The method steps include the step of generating a first thumbnail image including a graphical representation of basal rate profile data contained in a source file. The method further includes the step of, without opening the source file to access the data, displaying the first thumbnail image. The method further includes the step of opening the source file to access the data in response to an operator's selection of the first thumbnail image. The method further includes the step of replacing basal rate profile data contained in a target file stored on a pump with the data represented by the first thumbnail image. In this embodiment, the replacing step includes the step of displaying the first thumbnail image with a second thumbnail image including a graphical representation of the basal rate data contained in the target file to permit the operator to review differences between the images. In a variation thereof, the method steps further include the step of providing a dialog box for editing the data represented by the first thumbnail image. In another variation, the first thumbnail image includes a representation of twenty-four hourly basal rates on a graph having a time axis and a units per hour axis. In another variation, the method steps further include the step of displaying a file indicator with the first thumbnail image, the operator's selection including selection of the file indicator. In yet another variation, the first thumbnail image is displayed in a preview pane with a plurality of other thumbnail images corresponding to other basal rate profile data. In a still further variation, the replacing step further includes the step of displaying a critical change confirmation dialog box including the first and second thumbnail images when a daily basal insulin total represented by the first thumbnail image is greater than a daily basal insulin total represented by the second thumbnail image.

In another exemplary embodiment of the present disclosure, there is disclosed a system for programming an insulin pump. The system includes means for generating a first thumbnail image including a graphical representation of basal rate profile data contained in a source file. The system also includes means for displaying the first thumbnail image without opening the source file to access the data. The system also includes means for accessing the data in response to an operator's selection of the first thumbnail image. The system also includes means for replacing basal rate profile data contained in a target file stored on a pump with the data represented by the first thumbnail image. In this embodiment, the replacing means includes means for displaying the first thumbnail image with a second thumbnail image including a graphical representation of the basal rate data contained in the target file to permit the operator to review differences between the images.

BRIEF DESCRIPTION OF THE DRAWINGS

The above-mentioned aspects of the present teachings and the manner of obtaining them will become more apparent and the teachings will be better understood by reference to the following description of the embodiments taken in conjunction with the accompanying drawings, wherein.

DETAILED DESCRIPTION

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

It should be understood that although the concepts below are described as relating to insulin pump configuration software, such as the ACCU-CHEK® Insulin Pump Configuration Software provided by Roche Diagnostics Corporation, the concepts may also relate to diabetes management software systems for tracking and analyzing health data, such as, for example, the ACCU-CHEK® 360° product provided by Roche Diagnostics Corporation. Moreover, the concepts described herein may also have applicability to apparatuses, methods, systems, and software in fields that are unrelated to healthcare. Furthermore, it should be understood that references in this patent application to devices, pumps, meters, monitors, or related items are intended to encompass any currently existing or later developed apparatus that includes some or all of the features attributed to the referred to apparatus, including but not limited to the ACCU-CHEK® Active, ACCU-CHEK® Aviva, ACCU-CHEK® Compact, ACCU-CHEK® Compact Plus, ACCU-CHEK® Integra, ACCU-CHEK® Go, ACCU-CHEK® Performa, ACCU-CHEK® Spirit, ACCU-CHEK® D-Tron Plus, and ACCU-CHEK® Voicemate Plus, all provided by Roche Diagnostics Corporation or divisions thereof.

Figure 1:
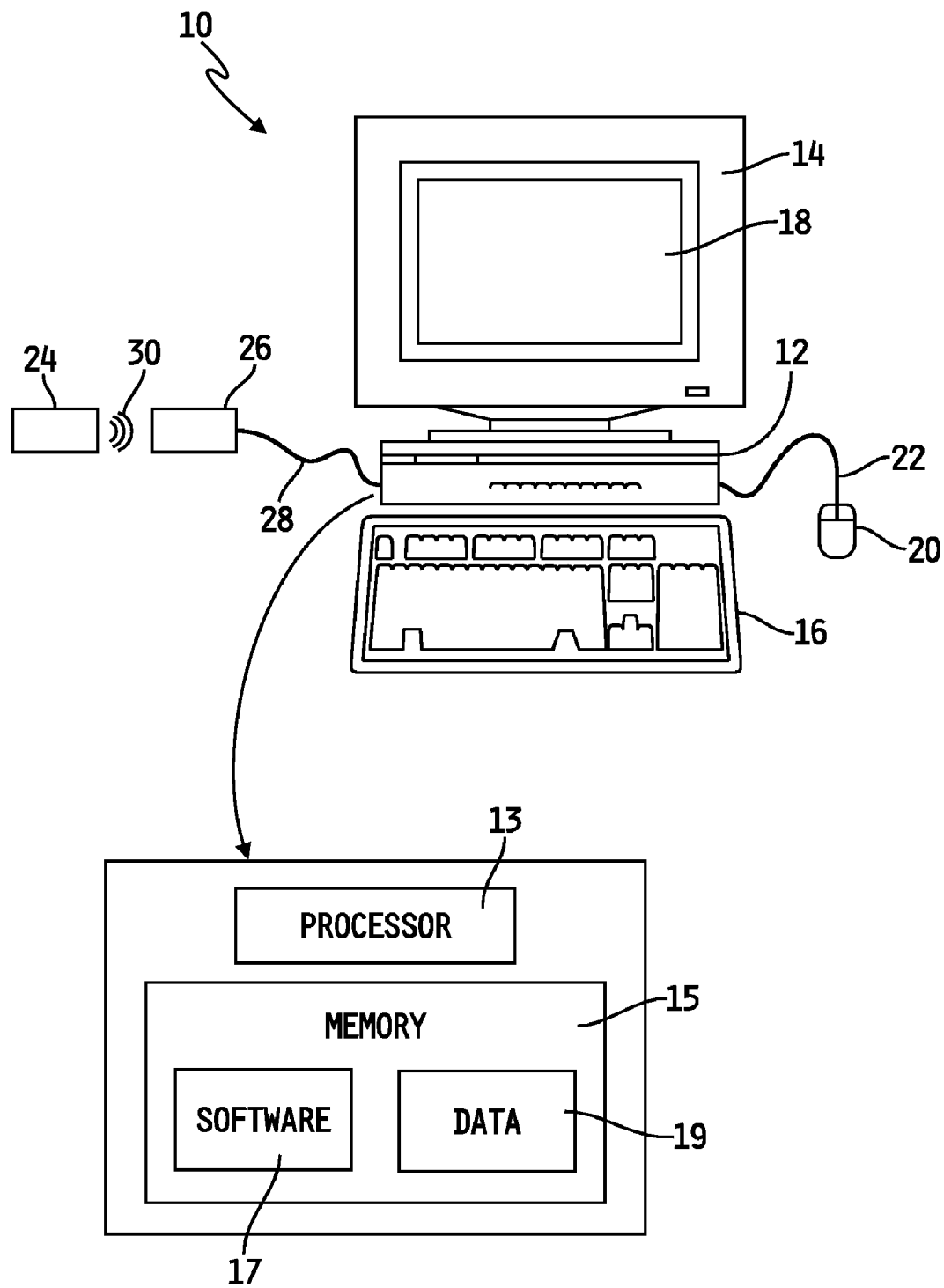
FIG. 1 is a conceptual diagram of a computing device in communication with an insulin pump.

Turning now to the figures, FIG. 1 depicts an exemplary embodiment of a system 10, some or all of the components of which may be used in conjunction with the teachings of the present disclosure. System 10 generally includes a computing device 12, shown here in the form of a computer having display device 14, in this case a computer video screen or monitor having screen 18, a keyboard 16, a processor 13, and memory 15, which may contain the software 17 of the present disclosure and data 19 as is further described herein. While described and depicted herein with specific reference to a computer, certain concepts of the present disclosure may be utilized in conjunction with any computing device capable of operating pump programming software. Computing device 12 also has a pointing device or mouse 20 connected to it by cable 22 (or wirelessly). While mouse 20 and keyboard 16 are shown, system 10 may include any input device such as a touchpad, joystick, touch screen, trackball, etc.

Computing device 12 may include a variety of computer-readable media. Computer-readable media can be any available media that can be accessed by computing device 12 and includes both volatile and non-volatile media, and removable and non-removable media. By way of example, and not limitation, computer-readable media may comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules and other data and which can be accessed by computing device 12. Computer-readable media may be accessed directly or through a network such as the Internet.

System 10 is configured to provide information to, and receive information from, infusion pump 24. Again, while an infusion pump, and more particularly an insulin pump, is described herein, it should be understood that the teachings of the present disclosure may also apply to devices such as "smart" insulin pens or other such devices known or hereafter developed. In FIG. 1, computing device 12 is shown coupled to communication media or dongle 26, in this case a modulated signal transceiver, accessible to computing device 12 by means of cable 28, and configured to transmit and receive modulated signal 30 to establish logical communication with pump 24. In another exemplary embodiment, computing device 12 and pump 24 may include ports configured to establish a physical connection. By way of example, and not limitation, dongle 26 may include wired media such as a wired network or direct wired connection, and wireless media such as acoustic, RF, infrared and other wireless media. More specifically, dongle 26 as depicted includes an infrared port for communication with a similar infrared port of pump 24.

Figure 2:
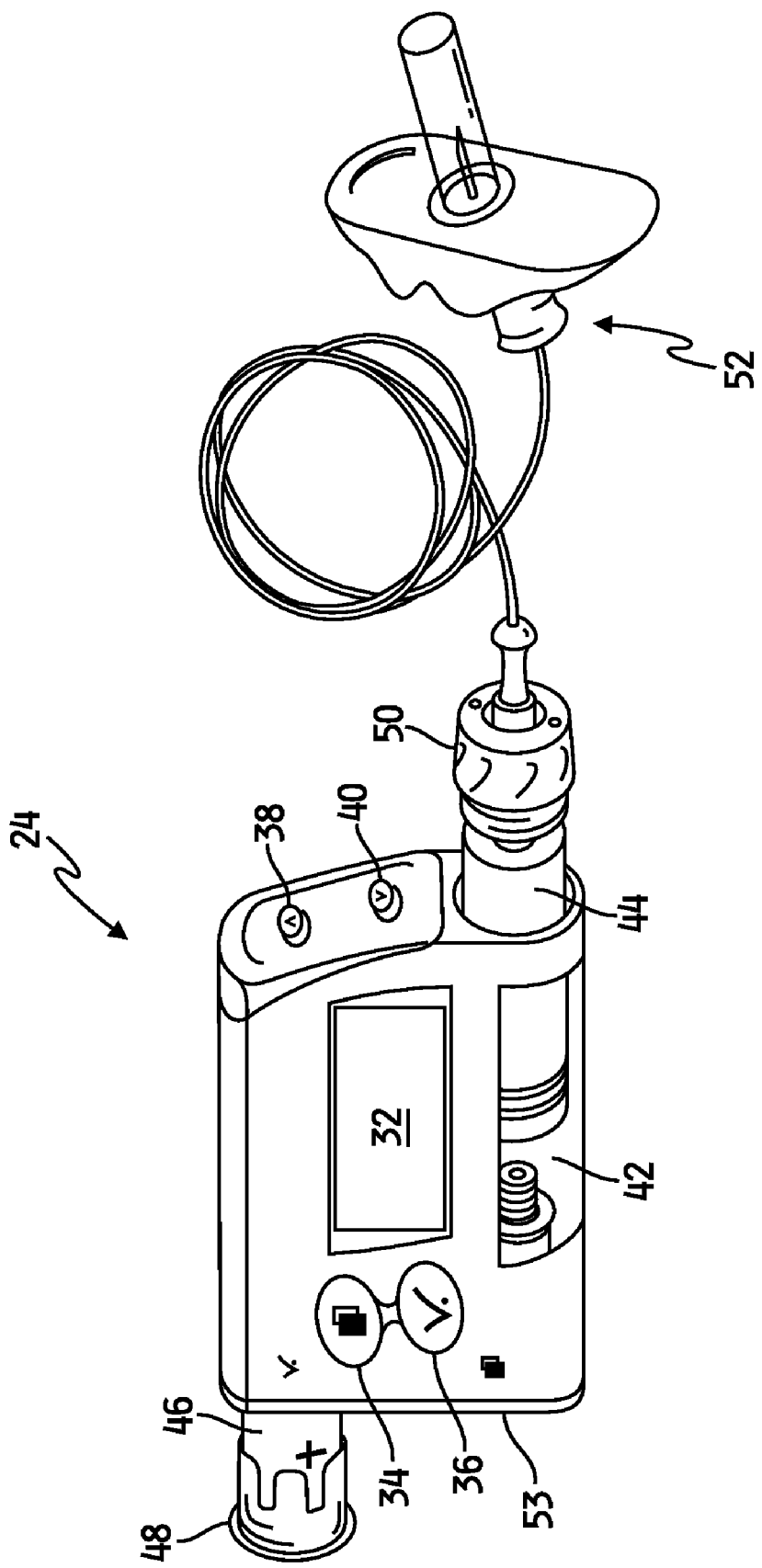
FIG. 2 is perspective view of an insulin pump coupled to an infusion set.

Referring now to FIG. 2, pump 24 includes a display 32 for displaying information to an operator or user, a menu button 34 for navigating though the various functions provided by pump 24, a check button 36 for selecting options, an up key 38 and down key 40 for scrolling through options and controlling certain insulin delivery functions, a cartridge receptacle 42 for storing an insulin cartridge 44, a battery 46 (shown partially inserted), a battery cap 48 (shown unsecured to pump 24), an adapter 50 for physically coupling cartridge 44 to an infusion set 52, and a communication port 53 for sending information to, or receiving information from, computing device 12 through dongle 26.

Figure 3:
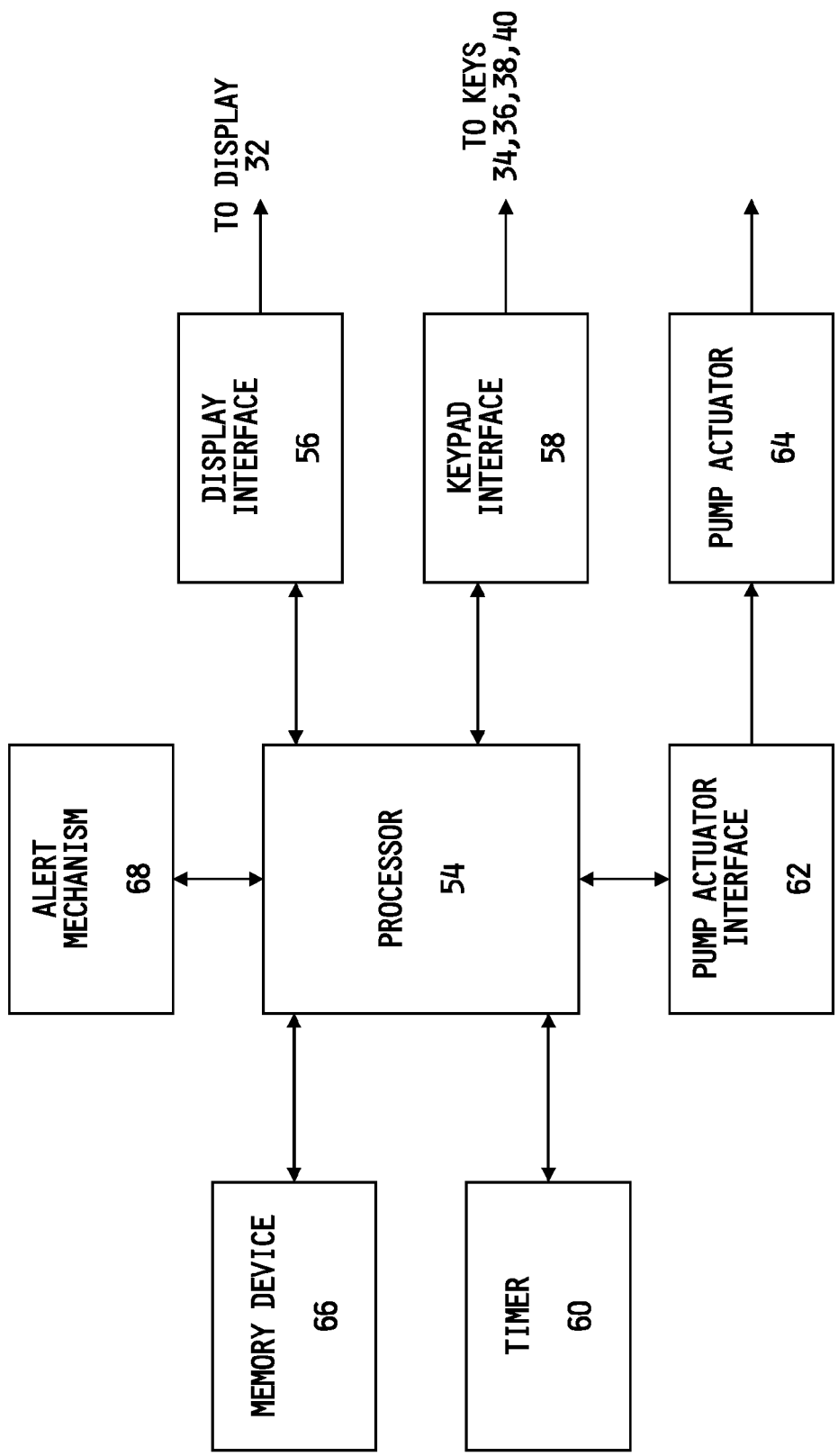
FIG. 3 is a block diagram of internal components of the pump of FIG. 2.

FIG. 3 provides a block diagram representation of internal components of pump 24. As shown, pump 24 includes a processor 54 coupled to a display interface 56, which is coupled to display 32. Processor 54 is also coupled to a keypad interface 58 which is coupled to keys 34, 36, 38, 40, and a pump actuator interface 62 which is coupled to an actuator 64 suitable for delivering insulin doses (medical infusion pumps other than insulin pumps will deliver doses of other medicament). Processor 54 is further coupled to a memory device 66 that stores application programs and data, including the configuration files described herein. Memory device 66 is constructed of any combination of volatile and/or nonvolatile memory suitable for a particular embodiment. Processor 54 is also coupled to an alert mechanism 68, that, in various embodiments is a buzzer, a vibrator, a light emitting diode, or the like, suitable for providing audible, tactile, or visual alerts to an insulin pump user. Finally, processor 54 is coupled to a timer 60, which is capable of maintaining a current time, including time of day and day of the week.

Figure 4:
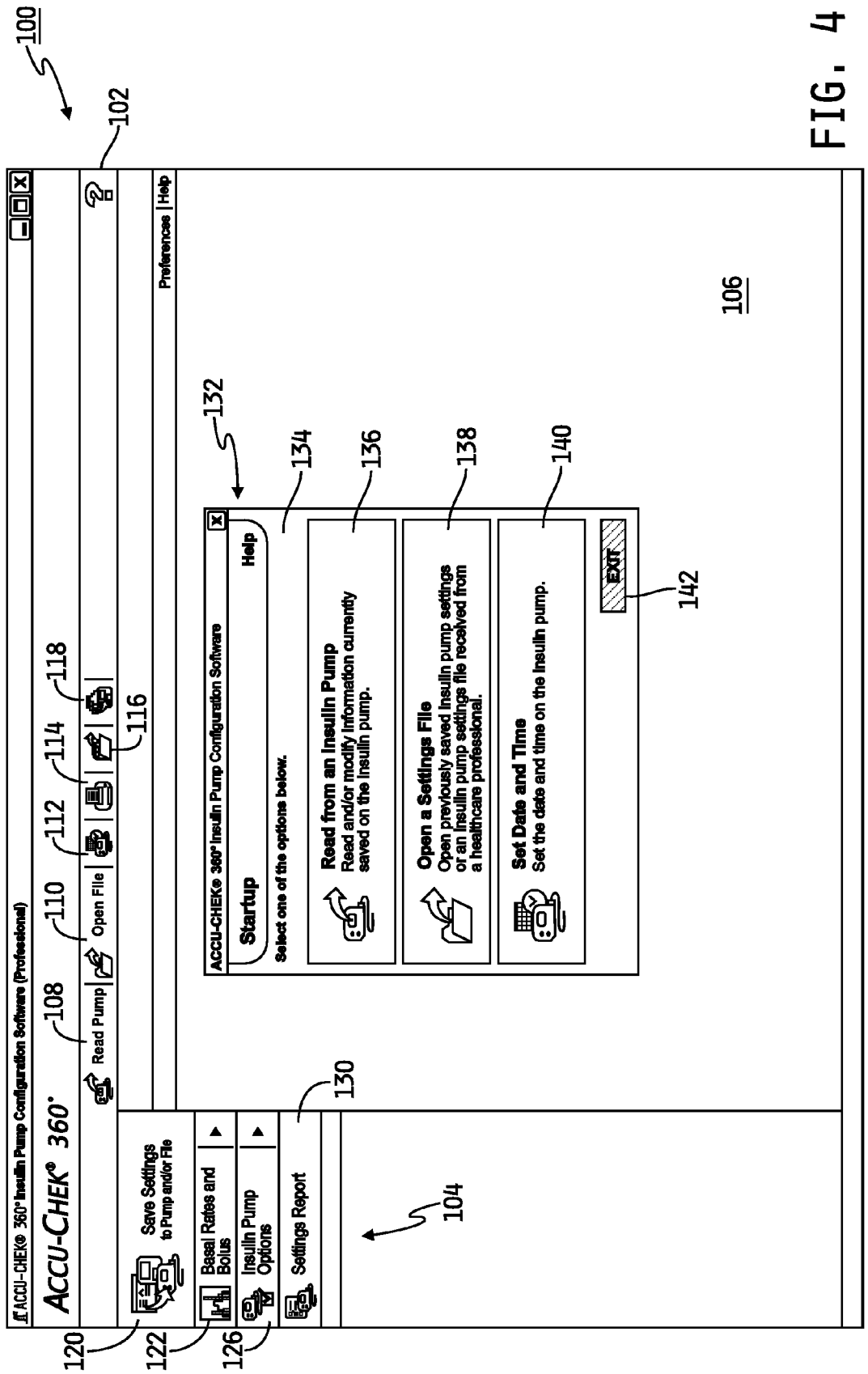
FIG. 4 is a screenshot of a home screen displayed upon activation of software according to teachings of the present disclosure.

FIG. 4 depicts the home screen 100 displayed upon activation of software 17. Home screen 100 generally includes a toolbar 102, a navigation menu 104, and an active window 106. Toolbar 102 includes a read pump icon 108, an open file icon 110, a date/time icon 112, a print icon 114, a load all profiles from file icon 116, and a save all profiles to a file icon 118. Navigation menu 104 includes a save settings button 120, a basal rates and bolus button 122, an insulin pump options button 126, and a setting report button 130. The content of active window 106 changes depending upon the operation being performed by software 17. Here, active window 106 includes a start up dialog box 132.

Start up dialog box 132 includes a message area 134, a read pump button 136, an open file button 138, a set date/time button 140, and an exit button 142. For the purpose of this description, the operator will be described as obtaining an insulin pump configuration file from memory 15 on computing device 12 using open file button 138. As is further described herein, the process for saving information to pump 24 or to memory 15 on computing device 12 differs. The process for obtaining or retrieving information from either pump 24 or memory 15 on computing device 12, however, is not meaningfully different for the purpose of the present disclosure.

Figure 5:
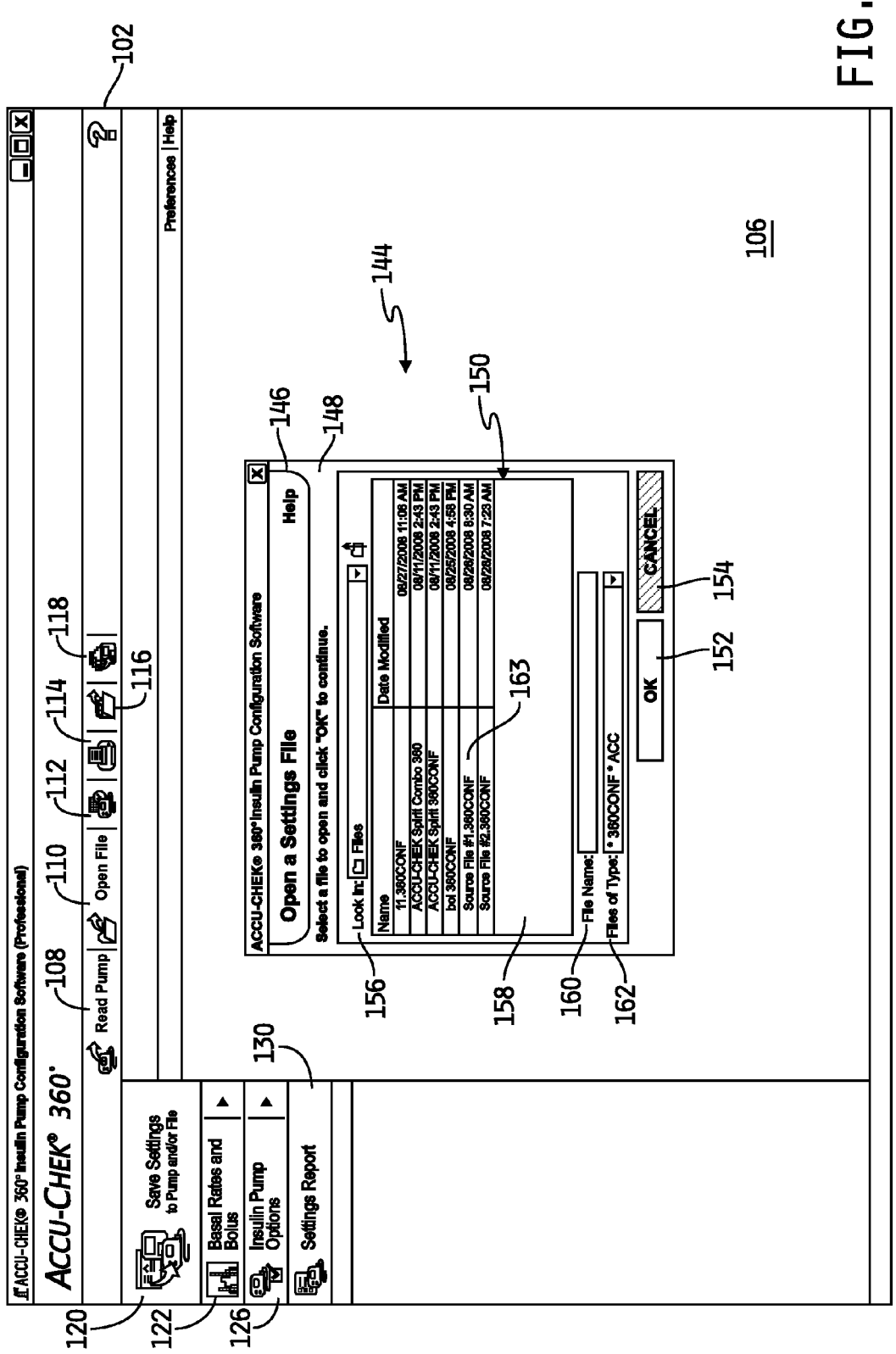
FIG. 5 is a screenshot including an open file dialog box.

As is shown in FIG. 5, when the operator activates open file button 138, start up dialog box 132 in active window 106 is replaced by open settings file dialog box 144. Open settings file dialog box 144 includes a title bar 146 which describes the operation being performed, a message area 148 which provides instructions to the operator for performing the operation, a file selection window 150, an OK button 152 and a cancel button 154. File selection window 150 includes a file location area 156 for defining a folder location of files using a conventional tree structure, a file information area 158 that provides information, including file indicators 163, about the files in the folder selected using file location area 156, a file name area 160 that includes the name of a file selected from file information area 158, and a file type area 162 for limiting, in a conventional manner, the types of files in the currently selected folder to be displayed in the file information area 158.

Figure 6:
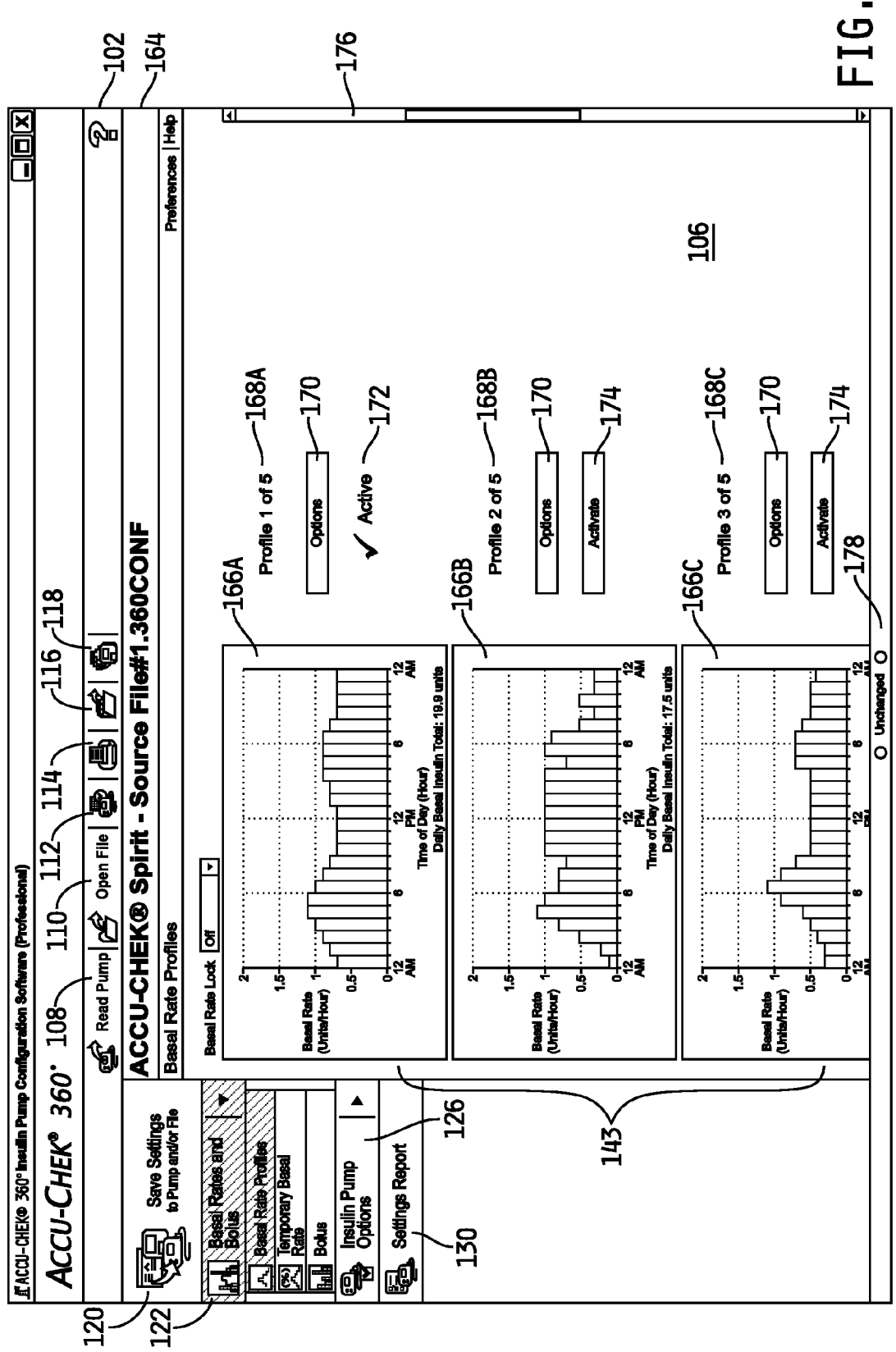
FIG. 6 is a screenshot of a display generated upon activating a configuration file.

In this example, the operator selects a configuration file named Source File #1.360CONF (hereinafter, "Source File #1") and activates OK button 152. After Source File #1 is retrieved from memory 15 of computing device 12, the operator is provided information in active window 106 regarding the basal rate profiles included in Source File #1 as depicted in FIG. 6. In the depicted context, active window 106 includes a title bar 164 that identifies Source File #1 as the active configuration file, a plurality of thumbnail images 166A-C that function as graphic previews of the data associated with the basal rate profiles included in Source File #1, a plurality of file indicators 168A-C indicating the number of the basal rate profile of the profile set in Source File #1 represented by the associated thumbnail image 166A-C, an options button 170 associated with each file indicator 168A-C, and either an active icon 172 or an activate button 174 associated with each file indicator 168A-C. Finally, active window 106 further includes a status bar 178 which indicates the status of the currently active configuration file. Here, the status is unchanged.

It should be understood that although portions of this description refer to hourly basal rate profiles, basal rates and basal rate profiles may cover more or less than a one hour time period. Indeed, the time periods covered by basal rates in a profile need not be equal. The concepts of the present disclosure are not limited by the duration of an individual basal rate, and the references to hourly basal rates are only exemplary.

In this example, Source File #1 includes a basal rate profile set 143 consisting of five individual basal rate profiles. Accordingly, as depicted in the figure, a thumbnail image 166A-C, profile designation 168A-C, options button 170, and active icon 172 or activate button 174 is displayed for each profile in profile set 143. In the description that follows, only the first three of the five possible basal rate profiles are used. The operator may view basal rate profile information not shown in active window 106 by using scroll bar 176. By default, the first listed profile is designated as active by software 17. As such, active icon 172 instead of activate button 174 is shown in association with thumbnail image 166A.

Although thumbnail image 166A is identified as "active," the data of the basal rate profile 1 (or any of the other profiles in profile set 143) is not yet loaded for editing. Thumbnail images 166A-C provide the operator the ability to see a simplified graphical representation of the underlying profiles without actually accessing the data. This simplifies the operator's task of locating and selecting a profile to edit during the programming operation.

Figure 7:
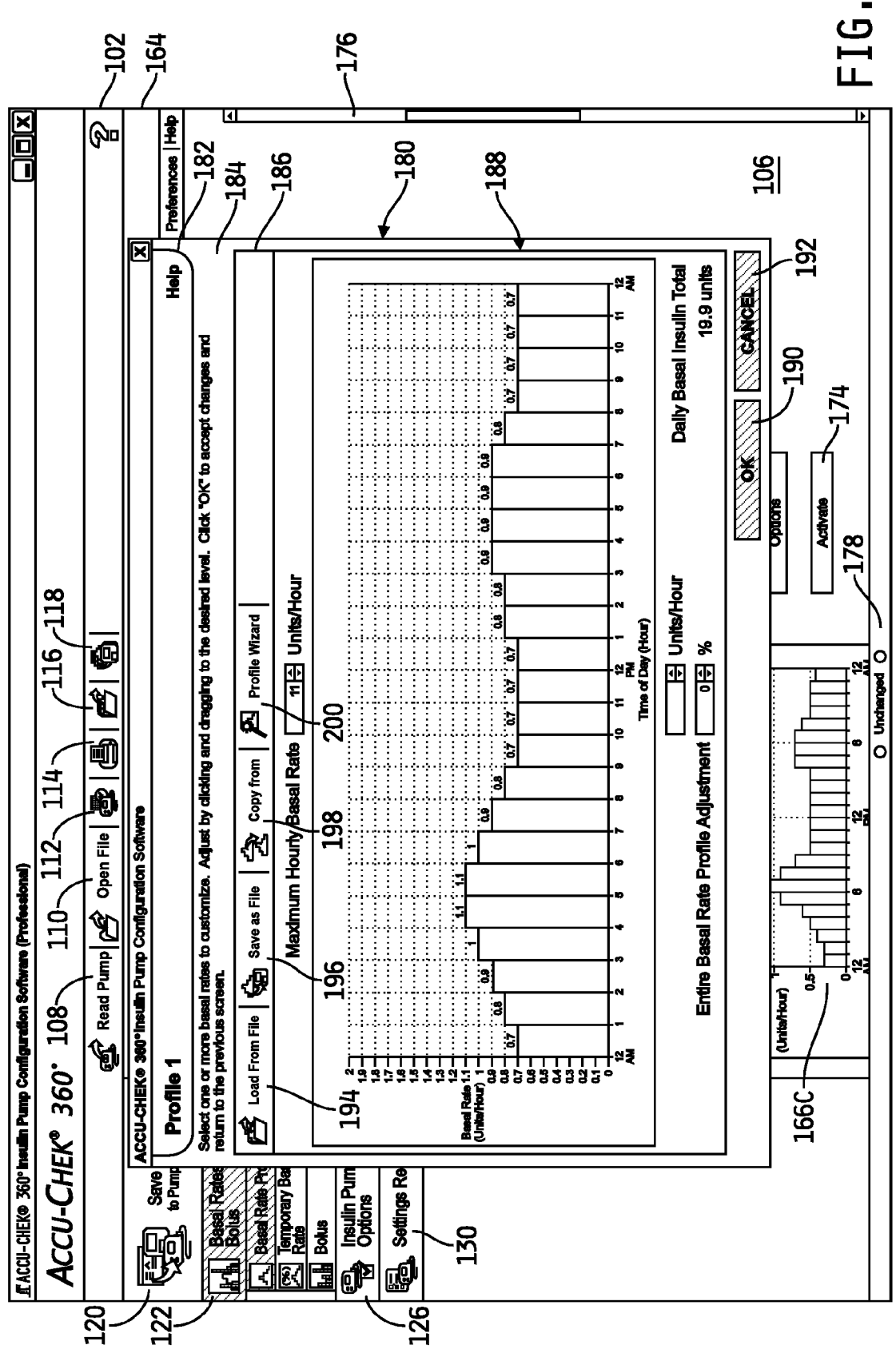
FIG. 7 is a screenshot of a display depicting a profile edit dialog box generated upon accessing a basal rate profile.

As shown in FIG. 7, when the operator activates options button 170 associated with profile 1 of 5, a profile edit dialog box 180 pops up over active area 106. At this point, the data associated with profile 1 has been accessed and used to populate dialog box 180. Profile edit dialog box 180 includes a title bar 182 that identifies the profile being edited, a message area 184 that provides information and instructions to the operator, a tool bar 186, a profile configuration window 188, an OK button 190 and a cancel button 192. Tool bar 186 includes a load from file button 194, a save as file button 196, a copy from button 198, and a profile wizard button 200. The basal rate profile data for a profile loaded in profile edit dialog box 180 may be modified in the manner described in co-pending patent applications entitled "USER INTERFACE FOR MANIPULATING GROUPS OF DATA REPRESENTATIONS OF A GRAPHICAL DISPLAY,", and "INSULIN PUMP CONFIGURATION PROGRAMMING INVALID SETTINGS NOTIFICATION AND CORRECTION,", (hereinafter, "the Invalid Settings Application"), the entire contents of which are hereby expressly incorporated herein by reference.

The above-mentioned simplification of thumbnail images can be appreciated by comparing thumbnail image 166A (FIG. 6) with the content of profile configuration window 188 (FIG. 7). As shown, the X and Y axis units are larger and the basal rate profile values provided in FIG. 7 are not included in thumbnail image 166A. When displayed in the context of FIG. 6, thumbnail image 166A does, however, include the daily basal insulin total associated with profile 1.

As indicated by the content of tool bar 186, profile edit dialog box 180 may be used to access profiles other than the profile made active using one of activate buttons 174 of FIG. 6. For example, profile 1 depicted in FIG. 7 may be replaced by loading another profile stored either on a pump or in memory 15 of computing device 12. For simplicity, only the process for loading a profile from memory 15 of computing device 12 is described herein.

Figure 8:
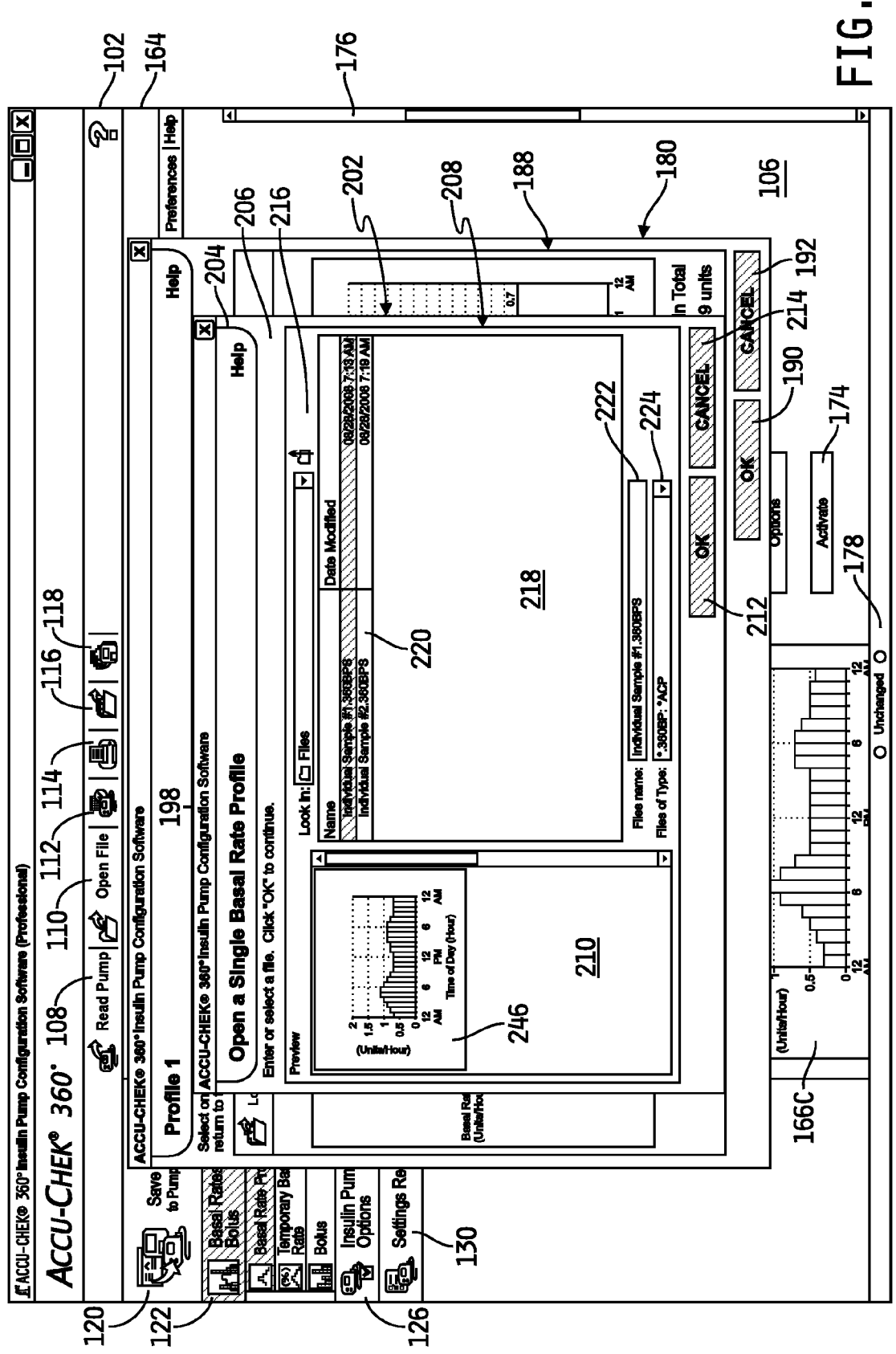
FIG. 8 is a screenshot including an open profile dialog box.

The operator may select another profile to populate profile edit dialog box 180 by activating load from file button 194 of tool bar 186. This causes software 17 to generate open profile dialog box 202 as depicted in FIG. 8. Dialog box 202 includes a title bar 204 describing the function of dialog box 202, a message area 206 that provides instructions to the operator, a file selection window 208, a preview pane 210, an OK button 212, and a cancel button 214. File selection window 208 includes a file location area 216, a file information area 218 that includes file indicators 220, a file name area 222, and a file type area 224. The functions of the various elements of file selection window 208 are similar to those described above with reference to file selection window 150 (FIG. 5).

As shown in FIG. 8, when a file indicator 220 in file information area 218 is highlighted such as by operator selection using a pointing device, a thumbnail image 226 corresponding to the underlying data of the profile associated with file indicator 220 is provided in preview pane 210. Thumbnail image 226 is similar to thumbnail images 166A-C described above. Accordingly, preview pane 210 (and thumbnail images 226 presented therein), permits the operator to browse through profiles by highlighting file indicators 220 and viewing thumbnail images 226 to locate a desired profile before selecting it. The operator may access the profile data underlying the selected profile by highlighting the appropriate file indicator 220 (which automatically populates file name area 222) and activating OK button 212 (or by double clicking file indicator 220). The newly selected profile will then populate profile edit dialog box 180 and may be edited or saved in the manner described herein.

Figure 9:
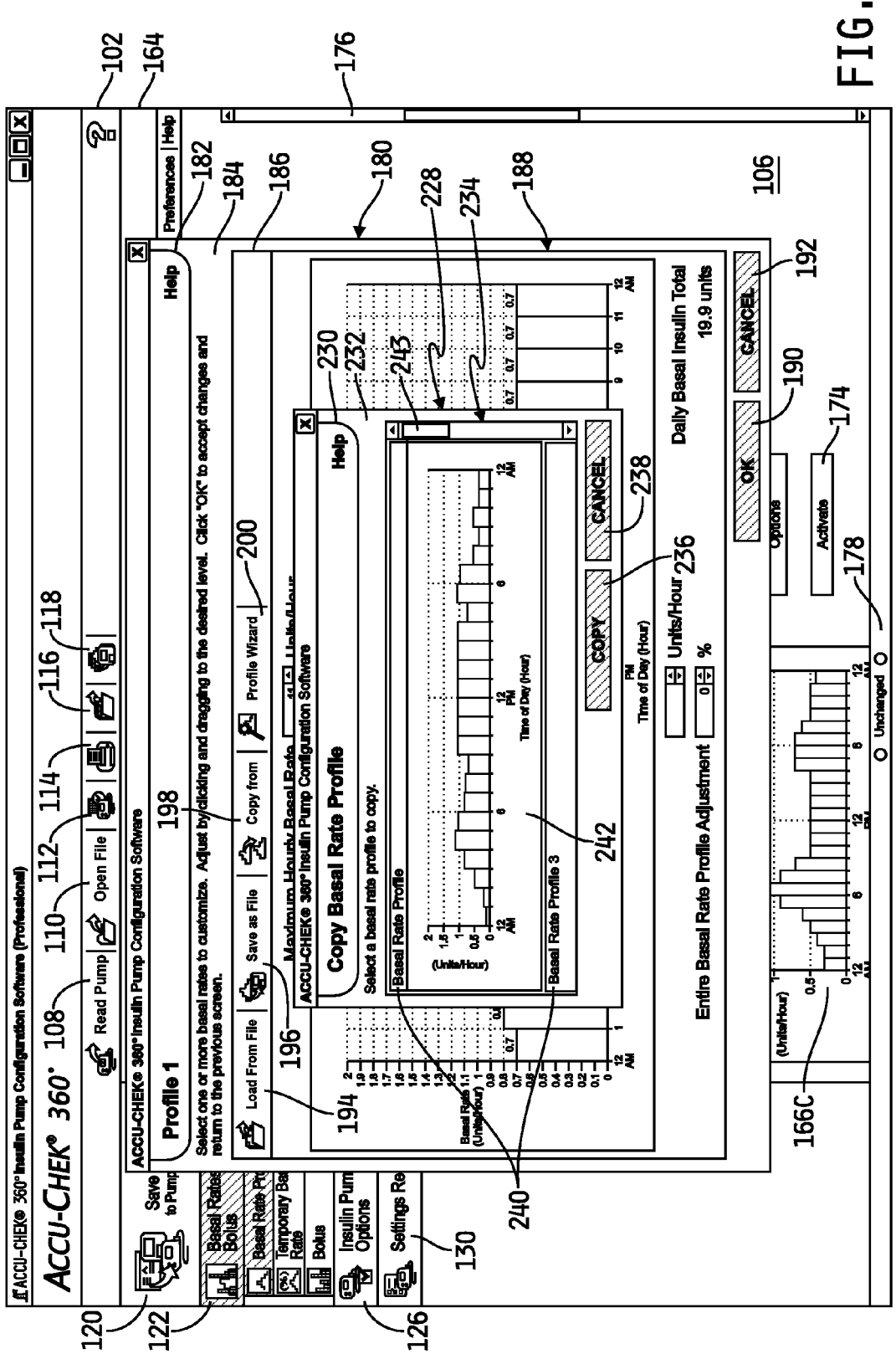
FIG. 9 is a screenshot including a copy profile dialog box.

Returning back to FIG. 7, instead of loading a new profile using load from file button 194, the operator may copy a predefined basal rate profile using copy from button 198. When the operator activates copy from button 198, software 17 generates a copy profile dialog box 228 as depicted in FIG. 9. Dialog box 228 includes a title bar 230, a message area 232, a preview pane 234, a copy button 236 and a cancel button 238. Preview pane 234 includes a plurality of file indicators 240 and associated thumbnail images 242, each pair corresponding to a profile stored in memory 15 of computing device 12. The operator can browse (using scrollbar 243) through the various thumbnail images 242 to located a desired profile without having to load the file and access the underlying data. When the operator locates a thumbnail image 242 that graphically represents the profile data desired by the operator, the operator may replace the currently active profile in profile edit dialog box 180 with the desired profile data by highlighting the selected thumbnail image 242 and activating copy button 236 (or by double clicking thumbnail image 242).

Figure 10:
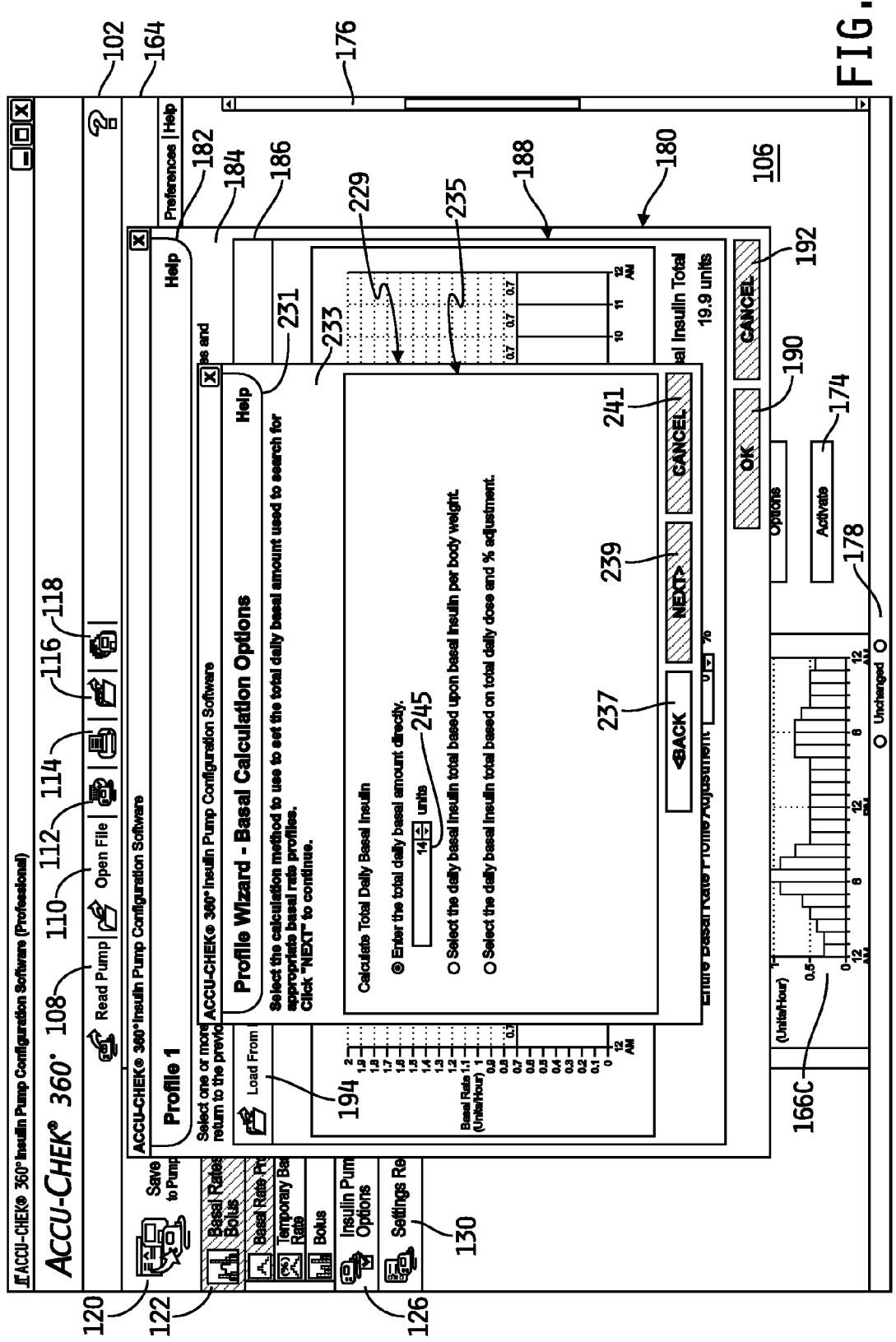
FIG. 10 is a screenshot including a basal options dialog box.

Returning again to FIG. 7, instead of loading a new profile using load from file button 194 or copying a profile using copy from button 198, the operator may generate and load a standardized profile using profile wizard button 200. When the operator activates profile wizard button 200, software 17 generates a basal options dialog box 229 as depicted in FIG. 10. Dialog box 229 includes a title bar 231, a message area 233, a calculation options window 235, a back button 237, a next button 239, and a cancel button 241. Calculation options window 235 includes radio buttons for selecting one of a plurality of different methods for computing a total daily basal insulin value to be applied to the standardized profiles described below. In the figure, the radio button for entering a value directly has already been selected, and the operator has entered the value 14 into text field 245. When the operator activates next button 239, software 17 generates a profile selection dialog box 247 as depicted in FIG. 11.

Figure 11:
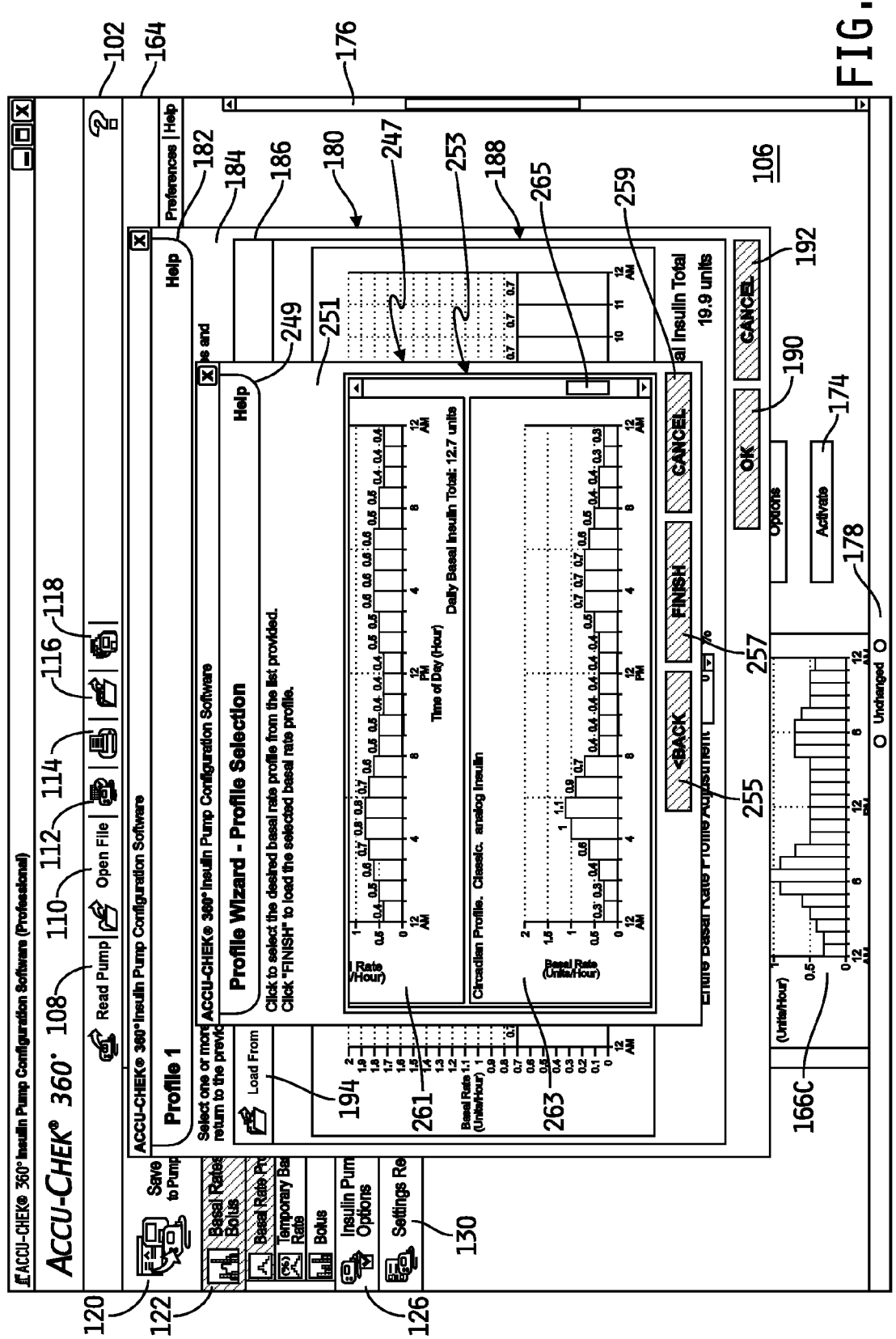
FIG. 11 is a screenshot including a profile selection dialog box.

As shown in FIG. 11, profile selection dialog box 247 includes a title bar 249, a message area 251, a preview pane 253, a back button 255, a finish button 257, and a cancel button 259. Preview pane 253 includes a plurality of thumbnail images (only two are shown—images 261 and 263), which are graphical representations of standardized profiles having basal rates that, when combined, remain within the previously defined total daily basal insulin value. For example, thumbnail image 263 represents a classic analog insulin circadian profile with a total daily basal insulin of less than 14. Using scrollbar 265, the operator can browse the various standardized profiles without having to load a profile to determine its contents. When the operator highlights a profile and activates finish button 257, the selected profile replaces the currently active profile populating profile edit dialog box 188.

Figure 12:
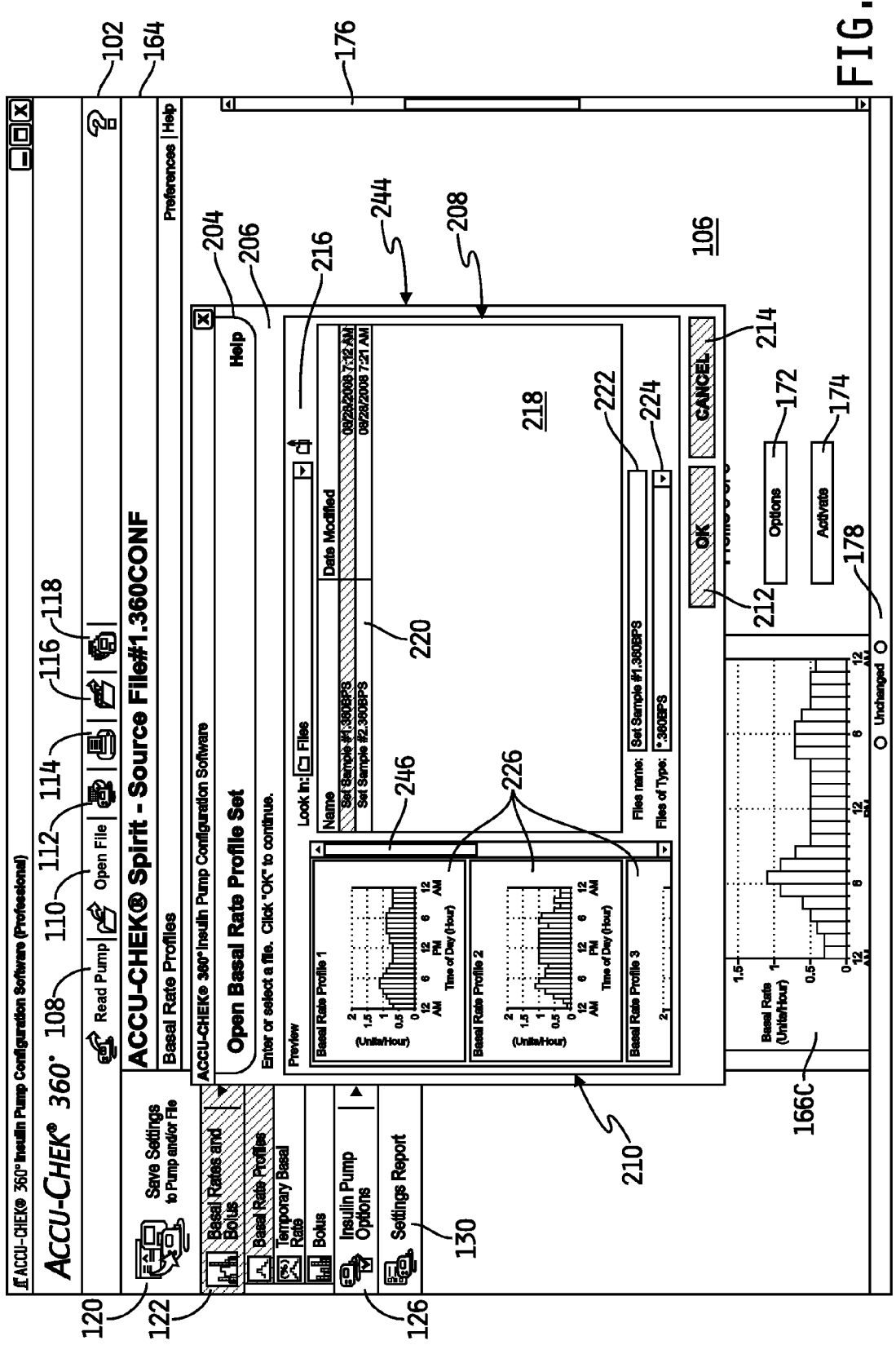
FIG. 12 is a screenshot including an open profile set dialog box.

Referring again to FIG. 6, instead of activating an options button 170 to access a profile, edit it, or load or copy a new profile as described above, the operator may replace profile set 143 with a different profile set in a single operation using load profile set button 116. When the operator activates load profile set button 116, software 17 generates an open profile set dialog box 244 as depicted in FIG. 12. Open profile set dialog box 244 is nearly identical to open profile dialog box 202 of FIG. 8. Accordingly, the same reference designations have been used in FIG. 12. Open profile set dialog box 244 is different, however, in that the files listed in file information area 218 include data representing entire sets of basal rate profiles instead of a single profile. Additionally, as the operator highlights file indicators 220 of file information area 218, preview pane 210 is populated with thumbnail images 226 of all of the profiles contained in the profile set corresponding to the highlighted file indicator 220. As such, preview pane 210 includes a scrollbar 246 to permit the operator to scroll through the thumbnail images 226 representing the profile set. Again, the operator can view a graphical representation of profiles without having to actually access the underlying profile data.

Figure 13:
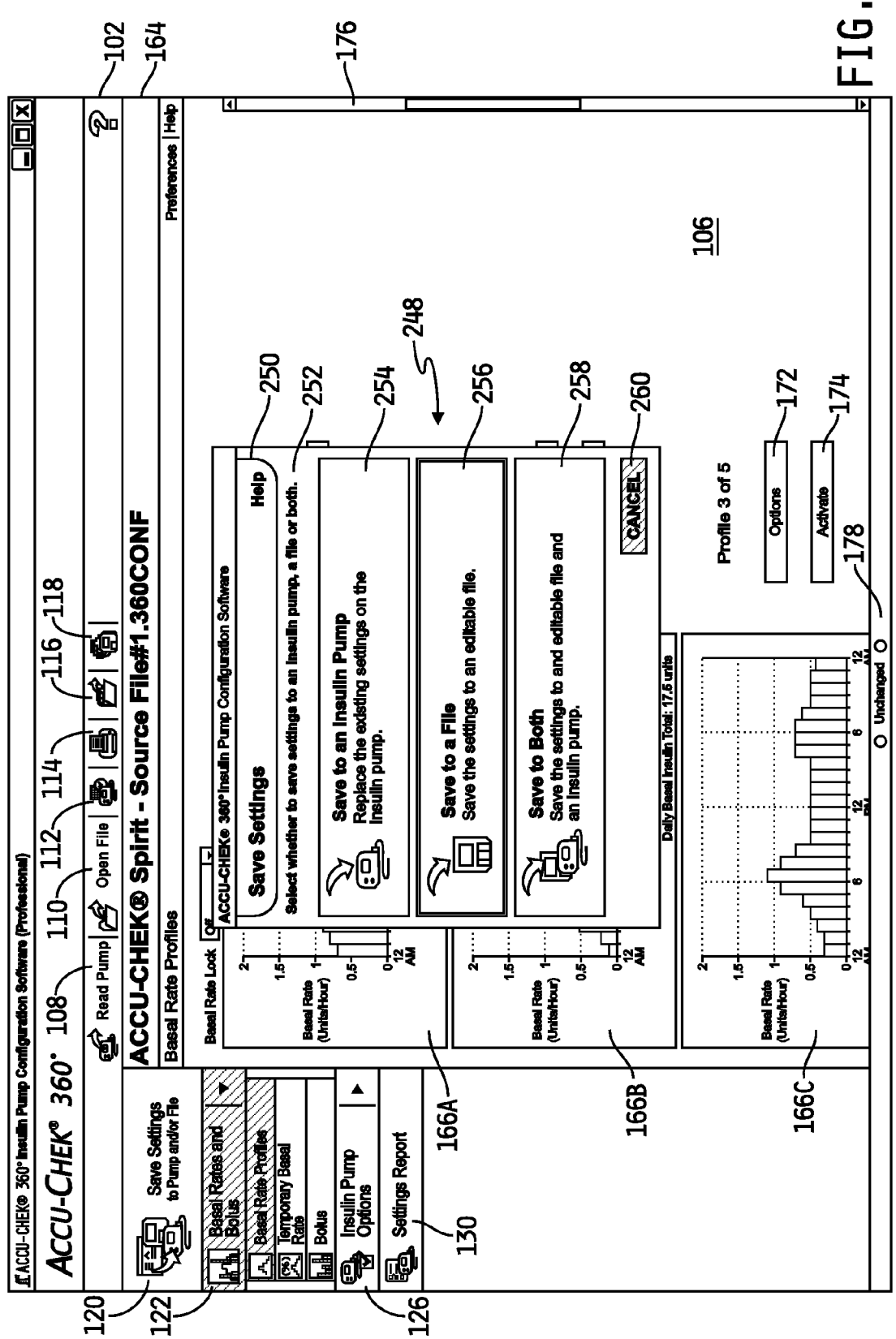
FIG. 13 is a screenshot including a save settings dialog box.

Preview features according to the principles of the present disclosure are also provided during save functions provided by software 17. Referring again to FIG. 6, after the operator has loaded (and perhaps edited) profile information (i.e., a configuration file, a profile set, or an individual profile), the operator may save that information to either a pump or a file using save settings button 120. When the operator activates save settings button 120, software 17 generates a save settings dialog box 248 as depicted in FIG. 13. In one embodiment, save setting dialog box 248 includes a title bar 250, a message area 252, a save to pump button 254, a save to file button 256, a save to both button 258 and a cancel button 260. Save to file button 256 permits the operator to save the currently loaded configuration file to memory 15 on computing device 12 in a conventional manner. Save to pump button 254 initiates a workflow that guides the operator through the process of replacing a configuration file present on a target pump. This process includes a plurality of safety features to assist the operator in avoiding errors during programming as are more fully described in the Invalid Settings Application and co-pending patent application entitled "INSULIN PUMP PROGRAMMING SOFTWARE FOR SELECTIVELY MODIFYING CONFIGURATION DATA,", (hereinafter, "the Selectively Modifying Application"), the entire contents of which are hereby expressly incorporated herein by reference. The following description primarily addresses only the thumbnail image preview features associated with the save to pump process.

Figure 14:
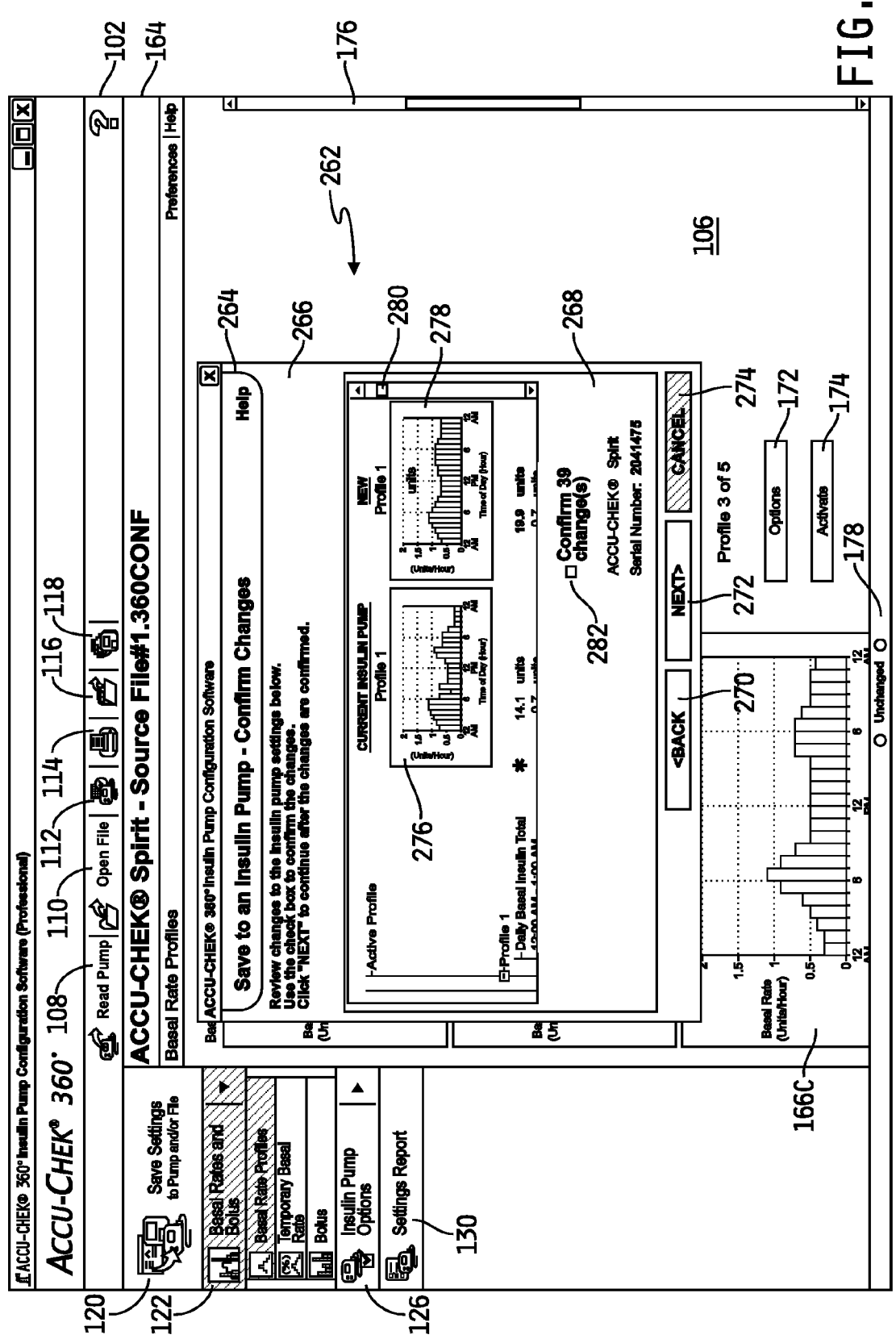
FIG. 14 is a screenshot wherein a communication status dialog box includes a comparison of information to be programmed on a pump and a confirm change box.

When the operator activates save to pump button 254, software 17 causes computing device 12 to communicate with pump 24 and ultimately generates a communications status dialog box 262 as depicted in FIG. 14. Dialog box 262 includes title bar 264, message area 266, status window 268, back button 270, next button 272, and cancel button 274. As fully described in the Selectively Modifying Application, status window 268 includes a variety of different kinds of information to assist the operator in determining that the intended changes will be made to the configuration file stored on pump 24. In general, status window 268 provides the operator with a summary of the changes that will be made to the pump configuration file upon completion of the programming operation. When a change is to be made to one or more profiles stored on pump 24, status window 268 provides at least one thumbnail image 276 of the profile currently residing on pump 24 and a thumbnail image 278 of the new profile that will replace the current profile. If more than one profile will be changed, the operator can use scrollbar 280 to view similar pairs of thumbnail images corresponding to the other profiles. In this manner, the operator is provided a graphical representation of the pending profile changes to assist the operator in verifying that the pending changes are what the operator intended.

Figure 15:
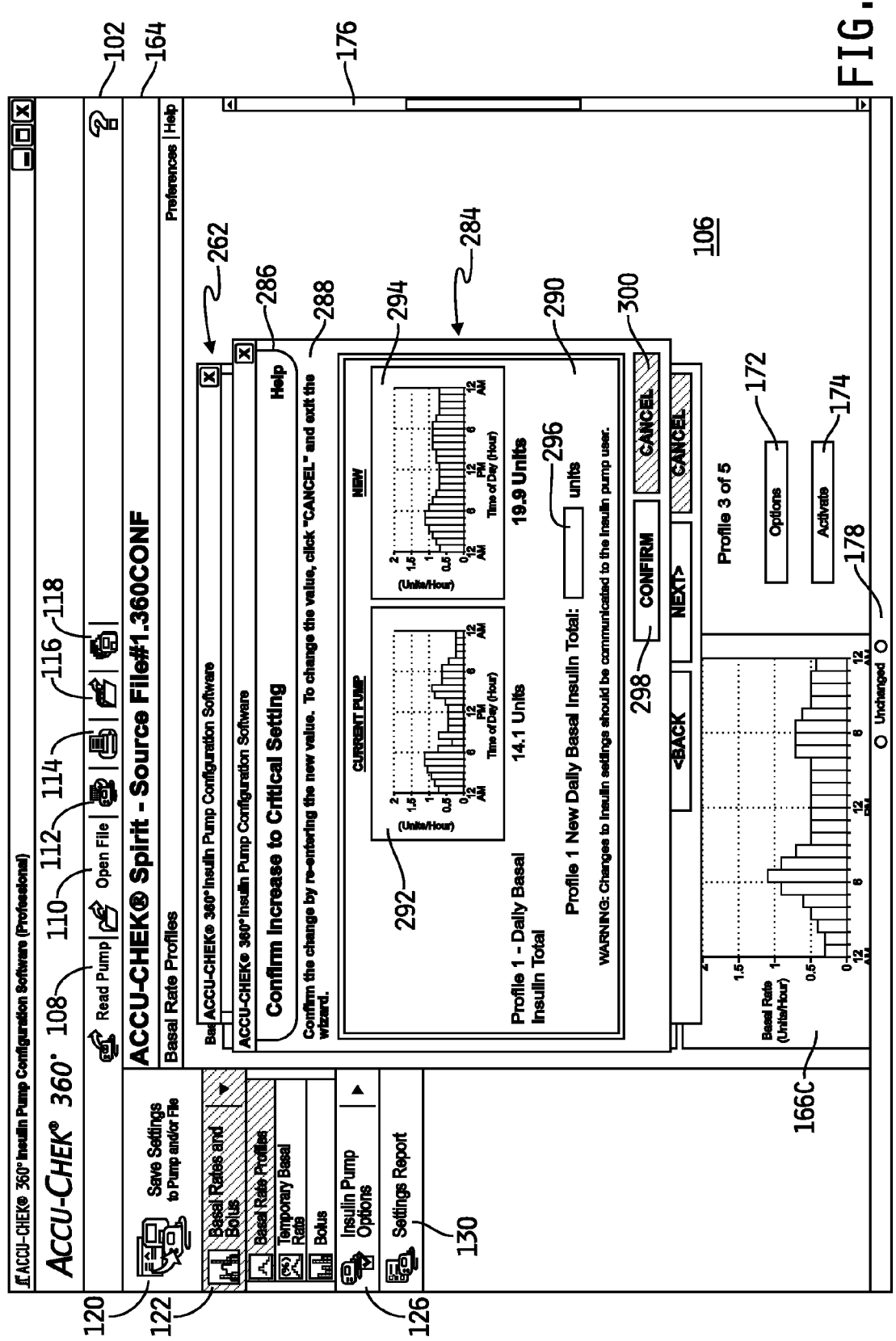
FIG. 15 is a screenshot including a critical change confirmation box for basal profile changes.

After the operator has reviewed the pending changes, the operator must check the confirm changes box 282 and activate next button 272 to proceed. In this example, the pending change to profile 1 of the pump's configuration file results in an increase in the daily basal insulin total associated with profile 1. As this type of change may have a direct adverse impact on the pump user's health if programmed by accident, software 17 requires a second confirmation step before programming the pump with the new profile as is further explained in the Selectively Modifying Application. Accordingly, when the operator activates next button 272 of FIG. 14, software 17 generates a critical change confirmation box 284 as depicted in FIG. 15.

Critical change confirmation box 284 includes a title bar 286, a message area 288 that instructs the user to re-enter the new data for the critical parameter about to be changed (here an increased daily basal insulin total), and a data window 290 including, among other things, thumbnail images 292, 294 which correspond to thumbnail images 276, 278 of FIG. 14, respectively, and a data field 296 for re-entry of the new data. Thumbnails 292, 294 provide yet another opportunity for the operator to compare graphical representations of the current and new profiles to visually confirm that the intended changes will be made by the programming operation. Box 284 also includes a confirm button 298 and a cancel button 300. Instead of requiring the operator to simply check a confirm changes box, which the operator may do without carefully reviewing the parameters being changed, critical change confirmation box 284 requires the operator to type the new data value exactly as it is shown in data window 290 and activate confirm button 298 to approve the change. In this example, the operator types 19.9 into data field 296 and activates confirm button 298 to proceed with the remainder of the programming operation.

As is described above, save setting dialog box 248 facilitates saving an entire configuration file. In an alternate embodiment, a save settings dialog box as disclosed in the Selectively Modifying Application is used, which permits saving configuration files, profile sets, or individual profiles to a pump. The principles of the present thumbnail image preview features may also be implemented in the processes for programming profile sets or individual profiles described therein.

While an exemplary embodiment incorporating the principles of the present teachings has been disclosed hereinabove, the present teachings are not limited to the disclosed embodiments. Instead, this application is intended to cover any variations, uses, or adaptations of the disclosed general principles. For instance, instead of having to load a profile to edit the underlying basal rate profile data, other software embodiments of the teachings of the present disclosure may facilitate profile editing by manipulating the thumbnail image of the profile. Further, this application is intended to cover such departures from the present disclosure as come within known or customary practice in the art to which this application pertains and which fall within the limits of the appended claims.

What is claimed is:

1. A method of managing basal rate profiles for use on an insulin pump, including the steps of:
    storing a file containing data corresponding to a basal rate profile for use by an insulin pump;
    generating a thumbnail image including a graphical representation of the profile;
    without opening the file to access the data, simultaneously displaying a file indicator associated with the file and the thumbnail image;
    determining based on the graphical representation of the thumbnail image whether to access the data; and
    opening the file to access the data in response to an operator's selection of the profile represented by the thumbnail image.

2. The method of claim 1, wherein the file is stored in a memory location of a computing device.

3. The method of claim 1, wherein the thumbnail image includes a representation of each basal rate in the profile on a graph having a time axis and a units per hour axis.

4. The method of claim 3, wherein the thumbnail image further includes a total daily basal insulin value.

5. The method of claim 1, wherein the file indicator includes a name of the file.

6. The method of claim 1, wherein the file is a configuration file including general configuration data and a plurality of basal rate profiles.

7. The method of claim 1, wherein the file is an individual basal rate profile file.

8. The method of claim 1, wherein the thumbnail image is displayed in a preview pane with a plurality of other thumbnail images corresponding to other basal rate profiles.

9. The method of claim 8, wherein the preview pane includes a scrollbar for browsing the plurality of thumbnail images.

10. The method of claim 1, wherein the generating step includes the step of receiving a basal insulin calculation input.

11. The method of claim 10, wherein the thumbnail image represents a standardized basal rate profile modified based on the basal insulin calculation input.

12. The method of claim 1, wherein the file is a profile set file including a plurality of basal rate profiles.

13. A method of programming basal rate profiles for use on an insulin pump, including the steps of:
    retrieving a source file including data corresponding to a first basal rate profile for use by an insulin pump;
    generating a first thumbnail image including a graphical representation of the first profile; and
    replacing a target file on an insulin pump corresponding to a second basal rate profile with the source file;
    wherein the replacing step includes the step of displaying the first thumbnail image with a second thumbnail image including a graphical representation of the second profile to permit an operator to review differences between the images and provide an input confirming a desire to complete the replacing step.

14. The method of claim 13, further including the step of modifying the source file.

15. The method of claim 13, wherein the replacing step further includes the step of displaying a critical change confirmation dialog box including the first and second thumbnail images when a daily basal insulin total corresponding to the first profile is greater than a daily basal insulin total corresponding to the second profile.

16. The method of claim 15, wherein the replacing step further includes the step of receiving a second input from the operator confirming a desire to complete the replacing step.

17. The method of claim 16, wherein the second input is a keyboard entry of the daily basal insulin total corresponding to the first profile.

18. A computer readable medium tangibly embodying a program of instructions executable by a computing device to perform method steps for programming insulin pumps, the method steps including:
    generating a first thumbnail image including a graphical representation of basal rate profile data contained in a source file;
    without opening the source file to access the data, displaying the first thumbnail image;

opening the source file to access the data in response to an operator's selection of the first thumbnail image; and replacing basal rate profile data contained in a target file stored on a pump with the data represented by the first thumbnail image;

wherein the replacing step includes the step of displaying the first thumbnail image with a second thumbnail image including a graphical representation of the basal rate data contained in the target file to permit the operator to review differences between the images.

19. The medium of claim 18, wherein the method steps further include the step of providing a dialog box for editing the data represented by the first thumbnail image.

20. The medium of claim 18, wherein the first thumbnail image includes a representation of twenty-four hourly basal rates on a graph having a time axis and a units per hour axis.

21. The medium of claim 18, wherein the method steps further include the step of displaying a file indicator with the first thumbnail image, the operator's selection including selection of the file indicator.

22. The medium of claim 18, wherein the first thumbnail image is displayed in a preview pane with a plurality of other thumbnail images corresponding to other basal rate profile data.

23. The medium of claim 18, wherein the replacing step further includes the step of displaying a critical change confirmation dialog box including the first and second thumbnail images when a daily basal insulin total represented by the first thumbnail image is greater than a daily basal insulin total represented by the second thumbnail image.

24. A system for programming an insulin pump, including:

means for generating a first thumbnail image including a graphical representation of basal rate profile data contained in a source file;

means for displaying the first thumbnail image without opening the source file to access the data;

means for accessing the data in response to an operator's selection of the first thumbnail image; and means for replacing basal rate profile data contained in a target file stored on a pump with the data represented by the first thumbnail image;

wherein the replacing means includes means for displaying the first thumbnail image with a second thumbnail image including a graphical representation of the basal rate data contained in the target file to permit the operator to review differences between the images.

\* \* \* \* \*